United States Patent
Mathys, Jr. et al.

(10) Patent No.: US 7,044,972 B2
(45) Date of Patent: May 16, 2006

(54) BONE IMPLANT, IN PARTICULAR, AN INTER-VERTEBRAL IMPLANT

(75) Inventors: Robert Mathys, Jr., Bettlach (CH); Beat Lechmann, Bettlach (CH); Beat Gasser, Ittigen (CH)

(73) Assignees: Synthes AG Chur, Chur (CH); Synthes (USA), Paoli, PA (US)

( * ) Notice: Subject to any disclaimer, the term of this patent is extended or adjusted under 35 U.S.C. 154(b) by 274 days.

(21) Appl. No.: 10/629,694

(22) Filed: Jul. 30, 2003

(65) Prior Publication Data

US 2004/0082999 A1    Apr. 29, 2004

Related U.S. Application Data

(63) Continuation of application No. PCT/CH01/00069, filed on Jan. 30, 2001.

(51) Int. Cl.
*A61F 2/44* (2006.01)

(52) U.S. Cl. .................. 623/17.16; 623/17.11

(58) Field of Classification Search .......... 623/17.11, 623/17.12, 17.13, 17.14, 17.15, 17.16
See application file for complete search history.

(56) References Cited

U.S. PATENT DOCUMENTS

| | | | | |
|---|---|---|---|---|
| 3,605,123 A | | 9/1971 | Hahn | 623/23.55 |
| 3,867,728 A | * | 2/1975 | Stubstad et al. | 623/17.16 |
| 4,062,834 A | * | 12/1977 | Gilding et al. | 521/149 |
| 4,911,718 A | * | 3/1990 | Lee et al. | 623/17.15 |
| 4,932,969 A | * | 6/1990 | Frey et al. | 623/17.12 |
| 5,192,327 A | * | 3/1993 | Brantigan | 623/17.11 |
| 5,607,424 A | * | 3/1997 | Tropiano | 606/61 |
| 5,888,227 A | | 3/1999 | Cottle | 623/17 |
| 6,773,460 B1 | * | 8/2004 | Jackson | 623/17.15 |
| 6,926,737 B1 | * | 8/2005 | Jackson | 623/17.16 |
| 2005/0101960 A1 | * | 5/2005 | Fiere et al. | 606/72 |
| 2005/0165489 A1 | * | 7/2005 | Michelson | 623/17.16 |

FOREIGN PATENT DOCUMENTS

| FR | 2742653 | 12/1995 |
|---|---|---|
| WO | WO 97/14377 | 4/1997 |
| WO | WO 00/66045 | 11/2000 |

* cited by examiner

*Primary Examiner*—Paul B. Prebilic
(74) *Attorney, Agent, or Firm*—Jones Day

(57) ABSTRACT

A bone implant and the method of manufacturing thereof, the bone implant, in particular an inter-vertebral implant, made of a radiation-permeable material having a circular-shaped hollow body with a sleeve. The inter-vertebral implant defining a surface and comprising a front section, a back section, and two lateral sections defining a central axis. The hollow body is subdivided by at least two partitions running essentially parallel to the central axis and which connect the front section to the back section. The surface of the bone implant has surface irregularities of at least 2 μm, and the at least two partitions have at least one perforation.

27 Claims, 1 Drawing Sheet

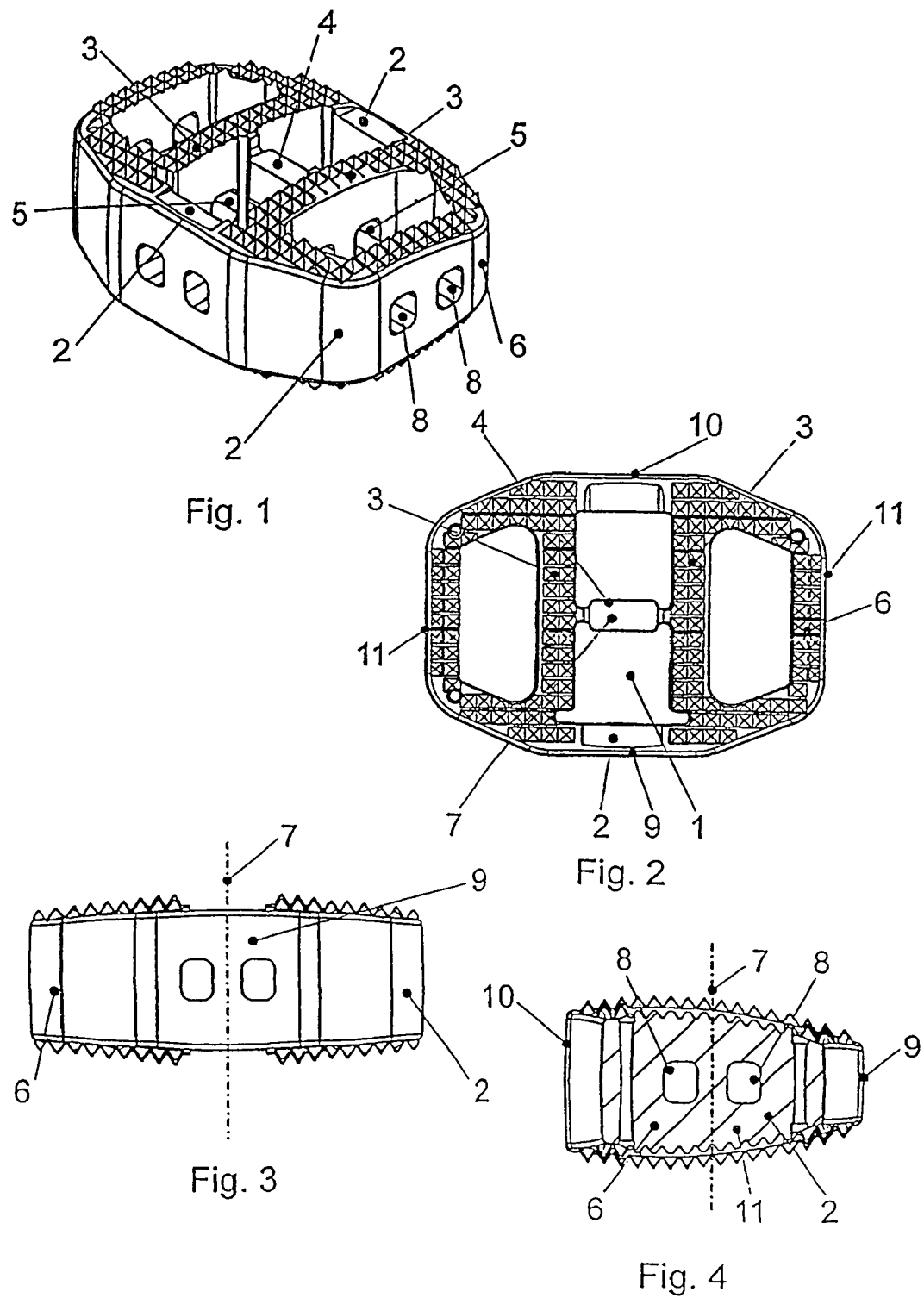

BONE IMPLANT, IN PARTICULAR, AN INTER-VERTEBRAL IMPLANT

CROSS-REFERENCE TO RELATED APPLICATIONS

The application is a continuation of the U.S. National Stage designation of copending International Patent Application PCT/CH01/00069, filed Jan. 30, 2001, the entire content of which is expressly incorporated herein by reference thereto.

BACKGROUND OF THE INVENTION

The present invention is directed to a bone implant, in particular an inter-vertebral implant as well as a method for producing the same.

Some of the disadvantages of bone implants known in the art are that: (i) the smooth surfaces of the top and bottom surface areas of the implant or those that are equipped with macroscopic serrations in contact with the base plates of the adjacent vertebrae, do not permit an optimal bone tissue growth; and (ii) where any bone growth filler is located in the hollow body of the implant, the filling easily comes out because of the smooth inner walls of the hollow body of the implant. Two publications disclosing bone implants having such characteristics are WO00/66045 to MICHELSON which is more specifically directed to spinal fusion implants with opposed locking screws and French Application 2 703 580 to ROBERT, is another type of bone implant, specifically directed to an intersomatic cervical cage.

SUMMARY OF THE INVENTION

The bone implant according to the present invention is directed to an inter-vertebral implant comprising an annularly shaped or circular hollow body, defined by an outer mantle or sleeve in the form of a hollow substantially cylindrical or cone section. The sleeve has a front section, a rear or back section, and two lateral sections which define a cylindrical or central axis. A portion of the front and back section may define a first pair of parallel walls while the two lateral sections may define a second pair of parallel walls. The hollow body may be subdivided by at least two partitions that run essentially parallel to the cylindrical axis and connect the front section to the rear section of the sleeve so as to further define superior and inferior support areas. The superior and inferior support areas preferably define opposed convex profiles. The partitions' walls increase the support areas on the neighboring vertebral bodies and plates, thereby reducing the surface pressure and preventing the implant from sinking into the neighboring vertebral bodies. In addition, the hollow spaces in between the partitions allow growth with the osseous structure through the implant. The surface of the bone implant has a surface roughness or irregularity of at least 2 µm, which affords the newly grown bone better fixation to the implant, and preferably the surface irregularities are less than 10 µm. The partitions preferably have perforations which preferably have a minimum area of 3.5 mm². In addition, the superior and inferior support areas may include pyramidal teeth for engaging the adjacent vertebral bodies.

In one embodiment of the bone implant, the partitions are trussed together by a cross strut or brace. Moreover, in a preferred embodiment, the lateral sections of the sleeve of the hollow body may have one or more perforations which preferably have a minimum area of 3.5 mm². The perforations in the lateral sections of the sleeve serve to spatially fix the newly grown osseous structure and also to provide primary support for the implant during insertion.

The bone implant may be made of a radiation transparent or permeable material. The bone implant may be made of radiation-permeable materials, wherein the material may be selected from the following group: polyarylether ketone (PAEK), polyetherimide (PEI), polyoxymethylene (POM), liquid-crystal polymer (LCP), polymethyl pentene (PMP), polysulfone (PSU), polyether sulfone (PESU or PES), polyethylene terephthalate (PETP), polymethyl methacrylate (PMMA), or ultra-high molecular weight polyethylene (UHMW-PE). All of these materials are elastic, but have various mechanical properties such as elasticity (stiffness) in addition to strength compared to other polymers, they sometimes have favorable creep properties or exhibit low water absorption. Moreover, the bone implant may be fiber-reinforced or strengthened with fibers. In yet another preferred embodiment, the fibers may be carbon fibers, glass fibers, or PEEK fibers.

The implant may be provided at least partially with an X-ray-transparent coating, or alternatively a thin coating such that the thin coating has little effect on the X-ray-transparency. The thin coating may additionally be made of metal, wherein a preferred embodiment, the thin coating is preferably titanium, or alternatively gold, or platinum. In another embodiment, the thin coating may be composed of ceramic material, preferably hydroxyapatite or alternatively tricalcium phosphate. The additional coating preferably enhances the mechanical properties and increases the interfaces between the implant and the newly grown bone.

In another embodiment of the bone implant, the ratio V:v between the total volume V of the bone implant and the volume v of the hollow body is in the range of 1.9 to 2.3. Moreover, the hollow body may be at least partially filled with a material made of calcium phosphate, preferably hydroxyapatite or alternatively tricalcium phosphate. In addition, the body, may be at least partially filled with material made of calcium sulfate, demineralized bone, autologous bone, or coralline substances. In another embodiment, the hollow body may be at least partially filled with an X-ray-opaque filler. The X-ray-opaque filler being made of a resorbable, preferably porous polymer. In order to design the filler to be X-ray-opaque, contrast medium may be added to the polymer. For PLA a marker, for example, such as zirconium dioxide, may be added, and barium sulfate may be admixed with PEEK. In another preferred embodiment, the perforations of the partitions, lateral sections or both may be filled with the X-ray-opaque filler thereby preventing the filler from falling out.

In a method of manufacturing a bone implant according to the present invention, the annular hollow body and preferably all form elements may be formed or manufactured by injection molding, hot forming, or hot pressing.

BRIEF DESCRIPTION OF THE DRAWINGS

Preferred features of the present invention are disclosed in the accompanying drawings, wherein similar reference characters denote similar elements throughout the several views, and wherein:

FIG. 1 is a perspective view of an illustrative embodiment of an inter-vertebral implant according to one aspect of the present invention;

FIG. 2 is a top view of the inter-vertebral implant of FIG. 1;

FIG. 3 is a front view of the inter-vertebral implant of FIG. 1; and

FIG. 4 is a side view of the inter-vertebral implant of FIG. 1.

DETAILED DESCRIPTION

Referring to FIGS. 1 through 4, there is shown an inter-vertebral implant configured for insertion between the adjacent vertebral endplates and permitting growth of an osseous structure through the implant. The inter-vertebral implant may be a generally annular or circular shaped hollow body 1 comprising a mantle or sleeve 6 defining a hollow cylindrical or cone section which has a front section 9, a rear section 10, and two lateral sections 11, and further defines a cylindrical or central axis 7. The hollow body 1 may be divided into chambers by at least two intermediate walls 3 running essentially or substantially parallel to cylindrical axis 7. The intermediate walls or partitions 3 connect front section 9 with back or rear section 10 of the sleeve 6, and may be supported, interconnected and spaced with respect to one another by at least one cross brace or strut 4. Intermediate walls 3 increase the support areas on the neighboring vertebral body endplates, thereby reducing the surface pressure and preventing the implant from sinking into the neighboring vertebral bodies. In addition, the chambers of hollow body 1 allow growth of an osseous structure through the implant. Moreover, each of intermediate walls 3 may be provided with at least one perforation 5 which may have an area of ranging from about 3.5 mm$^2$ to about 10 mm$^2$, preferably a minimum of about 3.5 mm$^2$. The perforations 5 in the intermediate walls 3 serve to spatially fix the newly grown osseous structure and also act as an optional area for primarily introducing a filling compound, which will be explained in greater detail below.

Lateral sections 11 of sleeve 6 may also have perforations 8, which have an area ranging from about 3.5 mm$^2$ to about 10 mm$^2$, preferably a minimum area of about 3.5 mm$^2$. The perforations in the lateral sections of the sleeve serve to spatially fix the newly grown osseous structure and also to provide primary support for the implant during its insertion. The perforations 8, may be similarly filled with a filling compound, to be explained in greater detail below.

A portion of the bone implant surface 2 may have a surface roughness. The surface roughness of surface 2 preferably ranges from 2 µm to about 10 µm, with a preferred minimum of 2 µm so as to provide newly grown bone tissue a better fixation to the implant, or better bone integration. An excessive surface roughness may impair the arthrodesis.

The inter-vertebral implant may be made from radiation-transparent material, preferably (PEEK), or alternatively, in another preferred embodiment, the radiation-transparent material may be made of: polyarylether ketone (PAEK), polyetherimide (PEI), polyoxymethylene (POM), liquid-crystal polymer (LCP), polymethyl pentene (PMP), polysulfone (PSU), polyether sulfone (PESU or PES), polyethylene terephthalate (PETP), polymethyl methacrylate (PMMA), or ultra-high molecular weight polyethylene (UHMW-PE). All of these preferred materials are elastic, but have various mechanical properties such as elasticity (stiffness) in addition to strength. Compared to other polymers, these preferred materials sometimes have favorable creep properties or exhibit low water absorption, therefore the material selected may depend upon the application requirements.

The radiation-transparent material of the bone implant may be fiber-reinforced, preferably with carbon or PEEK fibers. Fiber reinforcement of the radiation-transparent material enhances the mechanical properties of stiffness in general, or may provide a desired level of stiffness to the material.

Preferably, the surface 2 of the bone implant has a surface roughness of 6 µm and is at least partially provided with a thin, X-ray transparent coating, the coating preferably being metal and made of gold. Alternatively, the coating may have no effect on or may be so thin so as to have a negligible effect on radiation or X-ray transparency of the implant. Other thin metallic coatings are contemplated, for example titanium, platinum, or other appropriate implant metals are suitable. In another preferred refinement, the coating is made of a ceramic material, preferably hydroxyapatite or tricalcium phosphate. Both ceramics, hydroxyapatite and tricalcium phosphate, which are suited for a coating have the advantage that they become fully integrated into the bone, or are even replaced by new, natural bone tissue. Where the implant is made of pure PEEK, which is characterized by excellent biocompatibility, an additional coating made of a suitable material, such as the preferred metal material as described above, enhances the mechanical properties and increases the interfaces between the newly grown bone and the implant.

The ratio V:v between total volume V of the bone implant and volume v of the hollow body 1 is in the range of 1.9 to 2.3, preferably 2.1. It has been shown that this preferred ratio range combines the advantages of a mechanically stable implant with a maximum volume of newly grown osseous structure.

The hollow body 1 may be at least partially filled with a filler made of calcium phosphate, preferably hydroxyapatite or tricalcium phosphate, so as to provide better, more trouble-free monitoring of the arthrodesis. The hollow body may also be filled with a filler made of calcium sulfate, demineralized bone, autologous bone, or coralline substances.

Preferably, the hollow body 1 is filled at least partially with an X-ray-opaque filler made of a resorbable, preferably porous polymer. In order to design the filler to be X-ray-opaque, contrast medium may be added to the polymer. Where the filler polymer is PLA, a marker, for example, such as zirconium dioxide, may be added, and barium sulfate may be admixed with PEEK.

As explained above, the perforations 5, 8 in the implant may be at least partially filled with X-ray-opaque filler, preferably the resorbable porous polymer as previously described. Placing the filler at least partially within the perforations 5, 8 should thus prevent the filler from falling out.

According to the method of manufacturing the bone implant as described above, the annular hollow body 1 may be manufactured by injection molding, hot forming, or hot pressing. The polymer may preferably be compressed by hot forming, which is characterized particularly by better fatigue strength.

One aspect of the current invention is to provide a bone implant, in particular an intervertebral implant, having an optimal surface structure for the growth of bone tissue.

While preferred embodiments and features of the present invention have been disclosed herein, it will be appreciated that numerous modifications and embodiments may be devised by those skilled in the art. It is intended that the appended claims cover all such modifications and embodiments as fall within the true spirit and scope of such claims and that the claims not be limited to or by such preferred embodiments or features.

What is claimed is:

1. An inter-vertebral implant made of a radiation-permeable material having a substantially circular-shaped hollow body with a sleeve, the inter-vertebral implant defining a surface and comprising:
a front section, a back section, and two lateral sections defining a central axis,
wherein the hollow body being subdivided by at least two partitions, the at least two partitions running essentially parallel to the central axis and connecting the front section to the back section and the at least two partitions have at least one perforation, and
wherein the perforations of the partitions are at least partially filled with an X-ray-opaque filler material.

2. The bone implant of claim 1, wherein the partitions are trussed together by a cross strut.

3. The bone implant of claim 1, wherein the perforations in each of the partitions have a minimum area of about 3.5 mm$^2$.

4. The bone implant of claim 1, wherein each of the two lateral sections have at least one perforation having a minimum area of about 3.5 mm$^2$.

5. The bone implant of claim 4, wherein the perforations of the two lateral sections are at least partially filled with an X-ray-opaque filler material.

6. The bone implant of claim 1, wherein the radiation-permeable material is formed from at least one of the group consisting of polyarylether ketone (PAEK), polyethermide (PEI), polyoxymethylene (POM), liquid-crystal polymer (LCP), polymethyl pentene (PMP), polysulfone (PSU), polyether sulfone (PESU or PES), polyethylene terephthalate (PETP), polymethyl methacrylate (PMMA), and ultra-high molecular polyethylene (UHMW-PE).

7. The bone implant of the claim 1, wherein the radiation-permeable material is strengthened with fibers, the fibers being at least one of the group selected from carbon fibers, glass fibers, and PEEK fibers.

8. The bone implant of claim 1 having a total volume, V, and the hollow body having a volume, v, and wherein the ratio of V:v between the total volume V of the bone implant and the volume v of the hollow body ranges from about 1.9 to about 2.3.

9. The bone implant of claim 1, wherein at least a portion of the surface has an X-ray-transparent coating.

10. The bone implant of claim 1, wherein at least a portion of the surface has a thin coating having substantially no effect on the X-ray-transparency.

11. The bone implant of claim 10, wherein the coating is made of a ceramic material, the ceramic material being hydroxyapatite or tricalcium phosphate.

12. The bone implant of claim 1, wherein the hollow body is at least partially filled with a filler material selected from at least one of the group consisting of calcium phosphate, hydroxyapatite, tricalcium phosphate, calcium sulfate, demineralized bone, autologous bone, coralline substances, and a resorbable polymer.

13. The bone implant of claim 12, wherein the polymer is substantially porous.

14. An inter-vertebral bone implant, made entirely or in part of a radiation-permeable material comprising a substantially circular-shaped hollow body with a sleeve, the inter-vertebral implant defining a surface and comprising:
a front section, a back section, and two lateral sections defining a central axis, the hollow body being subdivided by at least two partitions, the at least two partitions running essentially parallel to the central axis and connecting the front section to the back section, the at least two partitions trussed together by a cross strut,
wherein the at least two partitions have at least one perforation, and
wherein the perforations of the partitions are at least partially filled with an X-ray-opaque filler material.

15. The bone implant of claim 14, wherein the two lateral sections have at least one perforation.

16. The bone implant of claim 14, wherein the perforations have a minimum area of about 3.5 mm$^2$.

17. The bone implant of the claim 14, wherein the radiation-permeable material is strengthened with fibers.

18. The bone implant of claim 14, wherein at least a portion of the surface has a substantially X-ray-transparent coating.

19. The bone implant of claim 14, wherein the hollow body is filled at least partially with a filler made entirely or in part of a resorbable polymer.

20. An inter-vertebral implant, made entirely or in part of a radiation permeable material defining a surface, the implant comprising:
an outer sleeve defining a central chamber for receiving a filler material and configured for permitting new bone growth therethrough, the outer sleeve having a front section, a back section, and first and second lateral sections;
a first partition and a second partition, the first and second partitions connecting the front section to the back section so as to subdivide the central chamber, the first and second partitions spaced relative to one another and formed with the outer sleeve so as to define superior and inferior support areas for engaging and supporting endplates of inter-vertebral bodies adjacent said implant;
a plurality of perforations in the outer sleeve and the first and second partitions, the outer sleeve perforations in fluid communication with the central chamber for receiving and fixing the filler material with respect to the implant, and
wherein a cross brace is located between the first and second partitions for laterally supporting the first and second partitions and at least a portion of the surface has surface irregularities for fixation of the new bone growth.

21. The bone implant of claim 20, wherein the superior and inferior support areas define opposed convex profiles.

22. The bone implant of claim 21, wherein the superior and inferior support areas each have a first portion having pyramidal teeth for engaging an adjacent vertebral body.

23. The bone implant of claim 20, wherein the cross brace is located in the central chamber so as to be completely between the superior support area and the inferior support area.

24. The bone implant of claim 20, wherein a portion of the front section and a portion of the back section define parallel first and second walls, and a portion of the first lateral section and a portion of the second lateral section define parallel third and fourth walls, each of the first, second, third and fourth walls having perforations in communication with the central chamber.

25. The bone implant of claim 24, wherein the third and fourth parallel walls are substantially perpendicular to the first and second parallel walls.

26. The bone implant of claim 24, wherein the perforations of the partitions are substantially aligned with the perforations of the third and fourth walls.

27. The bone implant of claim 14 having a total volume, V, and the hollow body having a volume, v, and wherein the ratio of V:v between the total volume V of the bone implant and the volume v of the hollow body ranges from about 1.9 to about 2.3.

* * * * *